ent Number: 5,043,524
Date of Patent: Aug. 27, 1991

United States Patent [19]
Ryan

[54] SELECTIVE DOUBLE-BOND ISOMERIZATION PROCESS

[75] Inventor: Robert C. Ryan, Houston, Tex.

[73] Assignee: Shell Oil Company, Houston, Tex.

[21] Appl. No.: 558,371

[22] Filed: Jul. 27, 1990

[51] Int. Cl.$^5$ .............................................. C07C 5/23
[52] U.S. Cl. ................................................... 585/666
[58] Field of Search ....................... 585/666, 664, 671

[56] References Cited

U.S. PATENT DOCUMENTS

| | | | |
|---|---|---|---|
| 3,697,616 | 10/1972 | McDonough | 585/666 |
| 4,777,322 | 10/1988 | Hoelderich et al. | 585/666 |
| 4,992,613 | 2/1991 | Brownscombe | 585/666 |

OTHER PUBLICATIONS

Harrison et al., "Ionic and Metallic Clusters of the Alkali Metals in Zeolite Y", Journal of Solid State Chemistry, 54 330–341, 1984.

Martens et al., "Sodium Clusters in Zeolites as Active Sites for Carbanion Catalyzed Reactions", The Proceedings of the 7th International Zeolite Conference, 1986, 935–941.

Primary Examiner—Anthony McFarlane
Assistant Examiner—Nhat Phan

[57] ABSTRACT

This process selectively isomerizes the double-bonds of linear olefins without isomerizing the double-bonds of branched olefins. The process is carried out by contacting a mixture of linear olefins and branched olefins at a temperature ranging from about −10° C. to about 250° C. with a zeolite having an alkali metal deposited thereon.

12 Claims, No Drawings

SELECTIVE DOUBLE-BOND ISOMERIZATION PROCESS

FIELD OF THE INVENTION

This invention relates to a selective olefin double-bond isomerization process using a catalyst comprising zeolite and one or more alkali metals.

BACKGROUND OF THE INVENTION

Many petroleum process streams contain both straight-chain olefins and branched chain olefins. The straight-chain olefins and branched chain olefins each find different utilities in the chemical process industries. For example, the straight-chain olefins are frequently converted to alpha olefins which are then subsequently utilized to prepare detergent range alcohols or lubricating oil additives. Branched olefins can be utilized to prepare octane enhancers for gasolines and can also be utilized to prepare lubricating oil additives which have different properties than those prepared from straight-chain olefins. A process that would isomerize straight-chain alpha olefins in a mixture of straight-chain and branched chain alpha olefins would find commercial utility. For example, such a process when combined with an ethenolysis process could produce lower molecular weight straight-chain alpha olefins while leaving the branched chain alpha olefins untouched. A subsequent separation of the straight chain alpha olefins and the branched chain alpha olefins would result in two very useful process streams that could be converted to high value end products.

Methods are known in the art for preparing zeolites impregnated with alkali metals. Harrison et al in the *Journal of Solid State Chemistry* 54, 330–341 (1984) disclose a method for preparing sodium impregnated zeolites by heating the zeolites in sealed tubes containing alkali metals. Martens et al in *The Proceedings of the 7th International Zeolite Conference*-1986, p 935 et. seq., disclose a method for preparing sodium impregnated zeolites by impregnating the zeolites first with a solution of sodium azide following by heating to decompose the sodium azide to sodium metal. This latter reference also discloses the suitability of using the thus prepared zeolites for isomerizing normal butenes.

SUMMARY OF THE INVENTION

This invention relates to a process for the selective double-bond isomerization of linear olefins contained in a mixture of linear olefins and branched olefins without the contaminant double-bond isomerization of the branched olefins. Such a process comprises contacting at isomerization conditions the mixture of olefins with a catalyst comprising one or more alkali metals deposited on a zeolite. Preferably the zeolites contain micropores ranging from about 4 to about 12 angstroms and silica to alumina ratios of less than about 10.

DETAILED DESCRIPTION OF THE INVENTION

Isomerization Process

This invention provides a process for shifting the double-bond of straight chain olefins and not branched chain olefins by contact with a selective double-bond isomerization catalyst. Isomerization is carried out in a gas and/or liquid phase at isomerization conditions. Isomerization conditions typically include a temperature in the range of about $-10°$ C. to about $250°$ C., preferably from about $0°$ C. to about $100°$ C. Pressures will typically range from about atmospheric to about 50 bars, although pressures lower or high than these can be suitable utilized.

Olefins which are subject to the instant isomerization process typically include compounds having carbon numbers ranging from about $C_4$ to about $C_{100}$, preferably from about $C_6$ to about $C_{30}$, and more preferably from about $C_6$ to about $C_{20}$. The olefins may be contained in a substantially pure olefinic stream or the stream may contain other inert hydrocarbons such as alkanes or aromatics. The feed however should be substantially free of impurities such as water or acid which adversely effect the catalyst.

The process of the invention can be carried out either batchwise or continuously, using a fixed catalyst bed, or a stirred tank reactor or a fluidized bed or other mobile catalyst contacting processes as well as any other well-known contacting techniques. Preferred reaction conditions, e.g., temperature, pressure, flow rates, etc., vary somewhat depending on the specific type of reactor utilized, the catalyst composition, the particular feed olefins and the desired products. Contact times of the feed with the catalyst will depend upon the particular type of process utilized. For example, in a fixed bed reactor liquid hourly space velocities will typically range from 0.1 to about 20. For mobile catalyst contacting reactors, mean contact times can range from the order of seconds or less for fluidized beds up to hours, say 20 hours, for stirred tank reactors.

The Catalyst

The catalysts utilized in the instant process basically comprise zeolites which have been impregnated with alkali metals. As used herein the term "alkali metals" refers to the metals lithium, sodium, potassium, rubidium and/or cesium in the metallic or zero valent state.

Essentially any crystalline zeolitic aluminosilicate can be employed to prepare the catalysts utilized in the instant process. The zeolites can include both synthetic and naturally occurring zeolites. Illustrative of the synthetic zeolites are Zeolite X, U.S. Pat. Nos. 2,882,244; Zeolite Y, 3,130,007; Zeolite A, 2,882,243; Zeolite L, Bel. 575,117; Zeolite D, Can. 611,981; Zeolite R, 3,030,181; Zeolite S, 3,054,657; Zeolite T, 2,950,952; Zeolite Z, Can. 614,995; Zeolite E, Can. 636,931; Zeolite F, 2,995,358; Zeolite O, 3,140,252; Zeolite W, 3,008,803; Zeolite Q, 2,991,151; Zeolite M, 2,995,423; Zeolite H, 3,010,789; Zeolite J, 3,001,869; Zeolite W, 3,012,853; Zeolite KG, 3,056,654; Zeolite SL, Dutch 6,710,729; Zeolite Omega, Can. 817,915; Zeolite ZK-5, 3,247,195; Zeolite Beta, 3.308,069; Zeolite ZK-4, 3,314,752; Zeolite ZSM-5, 3,702,886; synthetic mordenite; the so-called ultrastable zeolites of U.S. Pat. Nos. 3,293,192 and 3,449,070; and the references cited therein, incorporated herein by reference. Other synthetic zeolites are described in the book "Zeolite Molecular Sieves-Structure, Chemistry and Use," by Donald W. Breck, 1974, John Wiley & Sons, incorporated by reference herein. Illustrative of the naturally occurring crystalline zeolites are analcime, bikitaite, edingtonite, epistilbite, levynite, dachiardite, erionite, faujasite, analcite, paulingite, noselite, ferrierite, heulandite, scolecite, stilbite, clinoptilolite, harmotone, phillipsite, brewsterite, flakite, datolite, chabazite, gmelinite, cancrinite, leucite, lazurite, scolecite, mesolite, ptilolite, mordenite, nepheline, natrolite, scapolite, thomsonite, gismondine, garronite, gonnardite, heulandite, laumontite, levynite, offretite, yugawaralite. Descriptions of certain naturally occurring zeolites are found in the aforementioned book by Breck, in the book "Molecular Sieves-Principles of Synthesis and Identification", R. Szostak, Van Nostrand Reinhold, New York, 1989, both incorporated by reference herein, and in other known references. These zeolites may be in the hydrogen form or may be partially or fully exchanged with ammonium or metal ions.

The particular type of zeolite utilized in the instant processes will depend, inter alia, on the feedstock being treated, availability of zeolite and the ease with which zeolite can be pretreated prior to the impregnation with the alkali metals.

Preferred zeolites will contain micropores having diameters ranging from about 4 to about 12 angstroms. The preferred zeolites will also have silica to alumina ratios of less than about 10. Zeolites with higher silica to alumina ratios are found to be less suitable than those with the lower silica to alumina ratios. It is postulated that the zeolites with the higher silica to alumina ratios have more acid sites that are harder to neutralize with the alkali metal, thus causing the catalyst selectivity to suffer. Particularly preferred zeolites are the faujasites, zeolites X and zeolites A. Particularly preferred among the faujasites are zeolites Y.

Any of the well-known means in the art can be utilized to impregnate the zeolites with alkali metals. For example, the vapor deposition, alkali metal azide decomposition and impregnation of molten alkali metals can all be suitable utilized. Impregnation with molten alkali metal(s) is a preferred catalyst preparative technique.

Prior to impregnation, the zeolite must be both treated to remove water and hydrogen ion exchange sites. The presence of hydrogen ions and water in the zeolite will cause it to react with sodium metal in an adverse fashion. Water is typically removed from zeolite by heating the zeolite at elevated temperatures in the presence of vacuum or a dried gas such as argon, nitrogen or air. Heating temperatures ranging from about 200°–600° C. are suitable for drying the zeolite. Hydrogen ions in the exchange sites are removed by ion exchange with suitable metal ions such as alkali metals ions, alkaline earth metal ions, transition metal ions or rare earth metal ions. Many commercially available zeolites are already in the fully ion-exchanged state such as calcium A and sodium Y zeolites.

In a typical preparative process the fully exchanged zeolite is heated at about 500° C. for about 1 to 20 hours in a nitrogen gas stream to remove all water. It is then cooled in a dry box and contacted with a suitable amount of molten alkali metal(s) to cause impregnation of the metal into the catalyst. Generally, the best catalysts are prepared by keeping the preparative temperatures as low as possible and not heating the subsequently prepared catalyst to high temperatures, particularly temperatures higher than that utilized in the isomerization process. The catalyst utilized in the instant process would typically contain alkali metal concentrations less than 75% by weight of the total catalyst, preferably less than about 60% by weight. Generally the alkali metal concentrations will range from greater than about 5% to less than 60% by weight of the total catalyst. From a functional point of view the amount of alkali metal impregnated into the zeolite should be not so great that the pores of the zeolite are plugged with alkali metal.

The ranges and limitations provided in the instant specification and claims are those which are believed to particular point out and distinctly claim the instant invention. It is, however, understood that other ranges and limitations that perform substantially the same function in substantially the same way to obtain the same or substantially the same result are intended to be within the scope of the instant invention as defined by the instant specification and claims.

The following illustrative embodiments are provided for illustration and are not to be construed as limiting the invention.

Catalyst Preparation

Sodium zeolite Y powder obtained from ALFA was pressed in a hydrostatic press at 15000 psi for 10 minutes and then crushed and sieved to 16–45 mesh. Approximately 40 grams of the zeolite were placed in a quartz tube and heated to about 475° C. under a flow of nitrogen (about 600 cubic centimeters per minute) for about 18 hours. The zeolite was then sealed under nitrogen and taken into a dry box. The zeolite was then admixed with the desired amount of cesium at the melting point of cesium.

The catalytic reactions were carried out at room temperature in the dry box utilizing a small stirred tank reactor. The alkali metal-containing zeolite and the olefins feedstock were placed in the reactor and stirred for approximately 22 hours. After reaction the catalyst was filtered from the olefin and the extent of isomerization was determined by gas chromatography. These results are shown in Table 1. For comparison purposes a reaction was carried out with sodium zeolite Y without alkali metal promotion. Similar experiments were carried out utilizing calcium zeolite A both with and without alkali metal promotion. These results are also shown in Table 1.

TABLE 1

| Catalyst Type and wt. % Cs | Double-Bond Isomerization of 50/50 Mixture of 1-hexene and 2,3-dimethyl-1-butene | |
|---|---|---|
| | Selectivity, wt % | |
| | 2-hexene | 2,3-dimethyl-2-butene |
| Cs/NaY - 5% | 0 | 0 |
| Cs/NaY - 9% | 15 | 0 |
| Cs/NaY - 23% | 8.9 | 0 |
| Cs/NaY - 33% | 0.8 | 0.1 |
| Cs/NaY - 52% | 6.4 | 0.2 |
| NaY - 0% | 0 | 0 |
| Cs/5A - 9% | 7 | 0 |
| 5A - 0% | 0 | 0 |

Catalysts were also prepared utilizing sodium metal and potassium metal and sodium zeolite 13X, calcium zeolite 5A and sodium zeolite Y and were also found to provide selective isomerization of straight chain olefins over branched chain olefins.

What is claimed is:

1. A process for the selective double-bond isomerization of linear olefins in a mixture of linear and branched olefins which comprises contacting at a temperature ranging from about −10° C. to about 250° C. said mixture with a catalyst comprising cesium in the metallic or zero valent state, deposited on a fully metal ion-exchanged zeolite.

2. The process of claim 1 wherein the temperature ranges from about 0° C. to about 100° C.

3. The process of claim 1 wherein the zeolite contains micropores having diameters ranging from about 4 to about 12 angstroms.

4. The process of claim 1 wherein the zeolite is selected from zeolites A, X, Y and mixtures thereof.

5. The process of claim 1 wherein the zeolite is faujasite.

6. The process of claim 1 wherein the catalyst is prepared by impregnating a fully metal ion-exchange zeolite, dried of water, with molten cesium.

7. The process of any one of claims 1-6 wherein cesium is present in an amount less than about 75 percent by weight of the total catalyst.

8. The process of any one of claims 1-6 wherein cesium is present in an amount less than about 60 percent by weight of the total catalyst.

9. The process of any one of claims 1-6 wherein cesium is present in an amount of greater than about 5 and less than about 60 percent by weight of the total catalyst.

10. The process of any one of claims 1-6 wherein the olefins have carbon numbers ranging from 4 to about 100.

11. The process of claim 10 wherein the carbon numbers range from about 6 to about 30.

12. The process of claim 11 wherein the carbon numbers range from about 6 to about 20.

* * * * *